(12) United States Patent
Lamberton et al.

(10) Patent No.: US 9,879,989 B2
(45) Date of Patent: Jan. 30, 2018

(54) METHODS AND SYSTEMS FOR INSPECTING A WIND TURBINE BLADE

(71) Applicant: General Electric Company, Schenectady, NY (US)

(72) Inventors: Gary Austin Lamberton, Glenville, NY (US); Curtis Wayne Rose, Mechanicville, NY (US)

(73) Assignee: General Electric Company, Schenectady, NY (US)

( * ) Notice: Subject to any disclaimer, the term of this patent is extended or adjusted under 35 U.S.C. 154(b) by 228 days.

(21) Appl. No.: 14/963,496

(22) Filed: Dec. 9, 2015

(65) Prior Publication Data

US 2017/0167863 A1 Jun. 15, 2017

(51) Int. Cl.
| | |
|---|---|
| *G01N 29/07* | (2006.01) |
| *G01B 17/02* | (2006.01) |
| *G01M 5/00* | (2006.01) |
| *G01N 29/04* | (2006.01) |
| *G01N 29/44* | (2006.01) |
| *F03D 17/00* | (2016.01) |

(52) U.S. Cl.
CPC ............ *G01B 17/02* (2013.01); *F03D 17/00* (2016.05); *G01M 5/0016* (2013.01); *G01N 29/043* (2013.01); *G01N 29/07* (2013.01); *G01N 29/4427* (2013.01); *G01N 2291/02854* (2013.01); *G01N 2291/048* (2013.01); *G01N 2291/103* (2013.01); *G01N 2291/2675* (2013.01); *G01N 2291/2693* (2013.01)

(58) Field of Classification Search
CPC . G01B 17/02; G01N 29/07; G01N 2291/2675
See application file for complete search history.

(56) References Cited

U.S. PATENT DOCUMENTS

| | | | |
|---|---|---|---|
| 2005/0132809 A1* | 6/2005 | Fleming | G01N 3/00 73/597 |
| 2011/0000302 A1* | 1/2011 | Deleye | G01N 29/07 73/637 |
| 2014/0363294 A1 | 12/2014 | Lamberton et al. | |

* cited by examiner

*Primary Examiner* — John Chapman, Jr.
(74) *Attorney, Agent, or Firm* — Armstrong Teasdale LLP

(57) ABSTRACT

A method of inspecting a connection joint including a first side coupled to an opposite second side along a bond, extending along an edge. The method includes generating at least one first sound wave at a first location on the first side, wherein the first location is at a first distance from the edge. The method also includes receiving the at least one first sound wave at a plurality of sensors coupled to the second side and determining that the bond is present at the first location. The method further includes generating at least one second sound wave at a second location on the first side, wherein the second location is offset a predetermined distance from the first location. The method also includes receiving the at least one second sound wave at the plurality of sensors and determining a width of the bond.

20 Claims, 7 Drawing Sheets

METHODS AND SYSTEMS FOR INSPECTING A WIND TURBINE BLADE

BACKGROUND

The field of the disclosure relates generally to wind turbines and, more particularly, to methods and systems for determining bond width on a wind turbine blade.

Turbine blades are the primary elements of wind turbines for converting wind energy into electrical energy. Known turbine blades have an airfoil cross-sectional profile such that, as air flows over the blade during operation, a pressure difference between a pressure side and a suction side of the blade is created, generating a lift force on the blade. The lift force generates torque on the main rotor shaft, that is coupled to a generator for producing electricity.

At least some known turbine blades consist of an upper (suction side) shell and a lower (pressure side) shell that are bonded together at joints along the trailing and leading edges of the blade. Generally, the edge joints are formed by applying a suitable bonding paste or compound along the edge joint such that a minimum designed bond width id defined between the shell members. To ensure the turbine blades will satisfy performance and lifecycle requirements, the width and the overall integrity of these adhesive bonds is frequently verified.

At least some known methods of inspecting the adhesive bond joints include visual inspection and/or non-destructive imaging inspection techniques such as ultrasonic testing and microwave inspection. However, at least some known turbine blade materials may be difficult to penetrate via ultrasound. Certain areas of the turbine blade may be obscured from ultrasonic testing because of the use of foam, balsa, or other types of core materials that do not allow ultrasonic frequencies to be easily transmitted therethrough. In addition, at least some known microwave inspection techniques may be limited by a potential for exposure to radiation.

BRIEF DESCRIPTION

In one aspect, a method of inspecting a connection joint including a first side coupled to an opposite second side along a bond, extending along an edge, is provided. The method includes generating at least one first sound wave at a first location on the first side, wherein the first location is at a first distance from the edge. The method also includes receiving the at least one first sound wave at a plurality of sensors coupled to the second side and determining that the bond is present at the first location. The method further includes generating at least one second sound wave at a second location on the first side, wherein the second location is offset a predetermined distance from the first location. The method also includes receiving the at least one second sound wave at the plurality of sensors and determining a width of the bond.

In a further aspect, a method of inspecting a wind turbine blade including a first side coupled to an opposite second side along a bond, extending along an edge, is provided. The method includes generating at least one first sound wave at a first location on the first side, wherein the first location is at a first distance substantially parallel to a chord direction from the edge. The method also includes receiving the at least one first sound wave at a plurality of sensors coupled to the second side, the plurality of sensors arranged in series along the chord direction, and determining that the bond is present at the first location. The determining that the bond is present includes calculating a theoretical thickness of the bond at the first location based on an output of the plurality of sensors in response to the at least one first sound wave and comparing a first cavity distance between the first side and second side at the first location to the theoretical thickness of the bond. Wherein if the theoretical thickness of the bond is approximately equal to the first cavity distance than the bond is present at the first location. The method further includes generating at least one second sound wave at a second location on the first side, wherein the second location is offset a predetermined distance in the chord direction from the first location. The method also includes receiving the at least one second sound wave at the plurality of sensors and determining a width of the bond. Wherein the determining the width of the bond includes calculating a theoretical thickness of the bond at the second location based on an output of the plurality of sensors in response to the at least one second sound wave. Comparing a second cavity distance between the first side and second side at the second location to the theoretical thickness of the bond, wherein if the theoretical thickness of the bond is different from the second cavity distance by greater than a threshold value than the bond is not present at the second location. Defining, at least partially, the width of the bond by the first distance when the bond is not present at the second location.

In another aspect, a system for inspecting a connection joint including a first side coupled to an opposite second side along a bond, extending along an edge, is provided. The system includes a sound wave device positioned at the first side and a plurality of sensors coupled to the second side. The system also includes a controller coupled to the sound wave device and the plurality of sensors. The controller is configured to generate at least one first sound wave from the sound wave device at a first location on the first side. The first location is at a first distance from the edge. The controller receives the at least one first sound wave at the plurality of sensors and determines that the bond is present at the first location. The controller is further configured to generate at least one second sound wave from the sound wave device at a second location on the first side, the second location is offset a predetermined distance from the first location. The controller receives the at least one second sound wave at the plurality of sensors and determines a width of the bond.

DRAWINGS

DETAILED DESCRIPTION

The exemplary bond width determination methods and systems described herein overcome at last some of the disadvantages associated with known methods and systems for use in determining bond width in wind turbine blades. The exemplary embodiments described herein include generating a sound wave that propagates through the turbine blade, receiving the sound wave at a plurality of sensors, and determining whether the bond is present at the sound wave location. For example, in one embodiment, a theoretical turbine blade thickness is calculated based on a travel time of the sound wave and compared to a measured thickness of the turbine blade. In some embodiments, a surface sound wave is removed with filtering such that a direct sound wave may be used for determining bond width. In each embodiment, the bond width determination methods and systems facilitate reducing costs associated with non-destructive testing of the wind turbine blade and provide a system that produces reliable results.

Unless otherwise indicated, approximating language, such as "generally," "substantially," and "about," as used herein indicates that the term so modified may apply to only an approximate degree, as would be recognized by one of ordinary skill in the art, rather than to an absolute or perfect degree. Approximating language may be applied to modify any quantitative representation that could permissibly vary without resulting in a change in the basic function to which it is related. Accordingly, a value modified by a term or terms, such as "about," "approximately," and "substantially," are not to be limited to the precise value specified. In at least some instances, the approximating language may correspond to the precision of an instrument for measuring the value. Here and throughout the specification and claims, range limitations may be identified. Such ranges may be combined and/or interchanged, and include all the sub-ranges contained therein unless context or language indicates otherwise.

Additionally, unless otherwise indicated, the terms "first," "second," etc. are used herein merely as labels, and are not intended to impose ordinal, positional, or hierarchical requirements on the items to which these terms refer. Moreover, reference to, for example, a "second" item does not require or preclude the existence of, for example, a "first" or lower-numbered item or a "third" or higher-numbered item.

Figure 1:
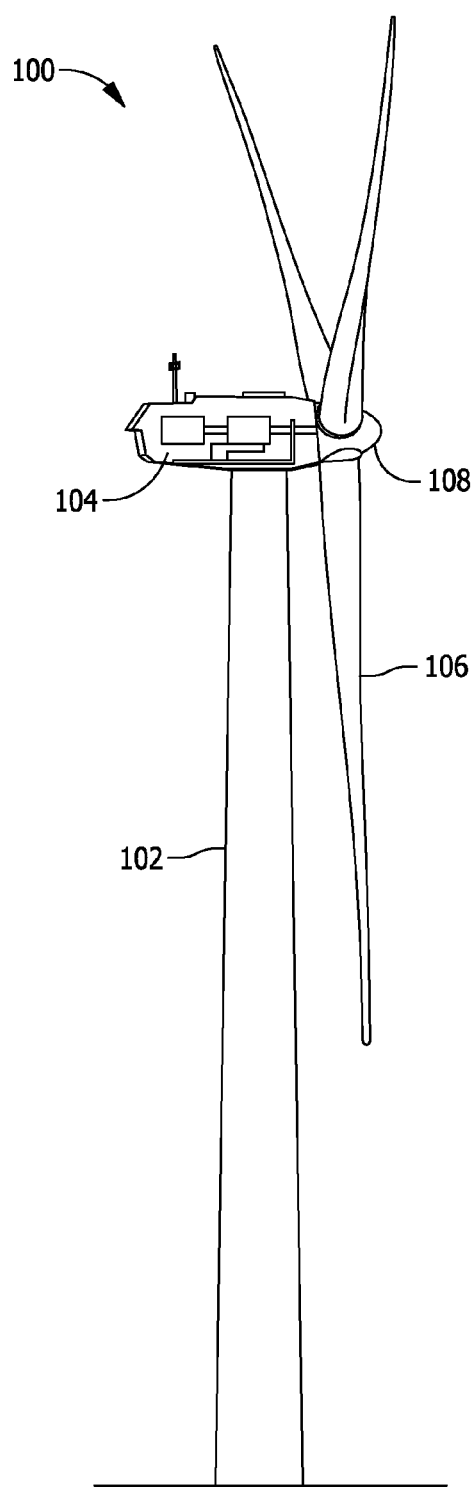
FIG. 1 is a perspective view of an exemplary wind turbine.

FIG. 1 is a perspective view of an exemplary wind turbine 100. In the exemplary embodiment, wind turbine 100 includes a tower 102 with a nacelle 104 coupled thereto. It should be noted that, as used herein, the term "couple" is not limited to a direct mechanical, electrical, and/or communication connection between components, but may also include an indirect mechanical, electrical, and/or communication connection between multiple components.

Furthermore, a plurality of turbine blades 106 are coupled to a rotor hub 108, which is in turn coupled to a main flange (not shown) that turns a main rotor shaft (not shown). The wind turbine power generation and control components are housed within nacelle 104. In operation, blades 106 have an airfoil cross-sectional profile such that, as air flows over blade 106, a pressure difference between a pressure side and a suction side is created, generating a lift force on blade 106. The lift force generates torque and rotates the main rotor shaft, which is geared to a generator (not shown) for producing energy. In alternative embodiments, wind turbine 100 has any other configuration that enables wind turbine 100 to operate as described herein.

Figure 2:
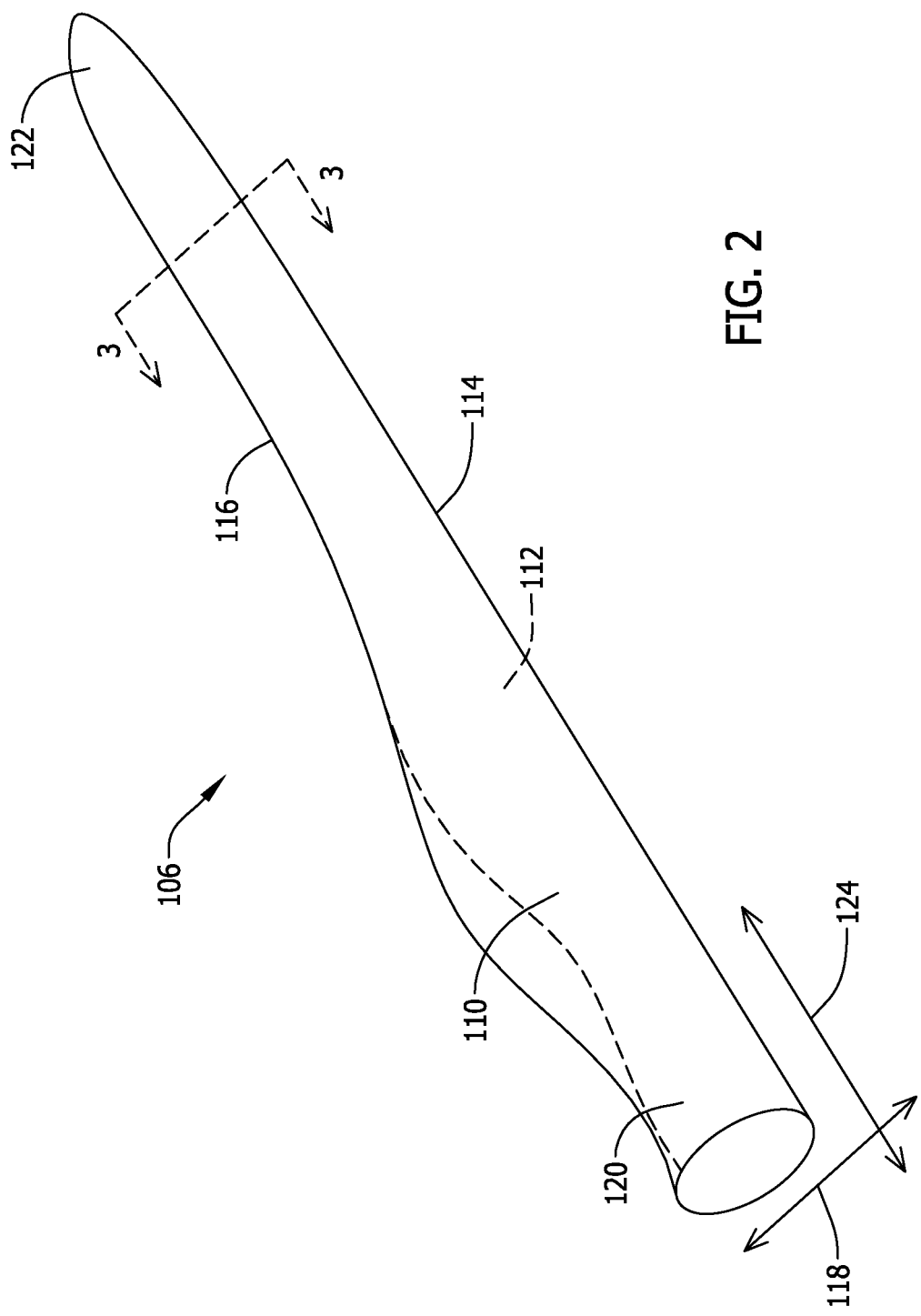
FIG. 2 is a perspective view of an exemplary blade that may be used with the wind turbine shown in FIG. 1.

FIG. 2 is a perspective view of an exemplary blade 106 of wind turbine 100 (shown in FIG. 1). In the exemplary embodiment, blade 106 includes a first member 110 coupled to a second member 112. More generally, in the exemplary embodiment, first member 110 is shaped as the suction side surface of blade 106, and second member 112 is shaped as the pressure side surface of blade 106. Blade 106 extends in a chord direction 118 from a leading edge 114 to a trailing edge 116. Additionally, blade 106 extends in a span direction 124 from a root portion 120 to a tip portion 122. In the exemplary embodiment, first and second members 110 and 112 are fabricated from core materials such as, but not limited to, foam, balsa, and/or engineered fiberboard.

Figure 3:
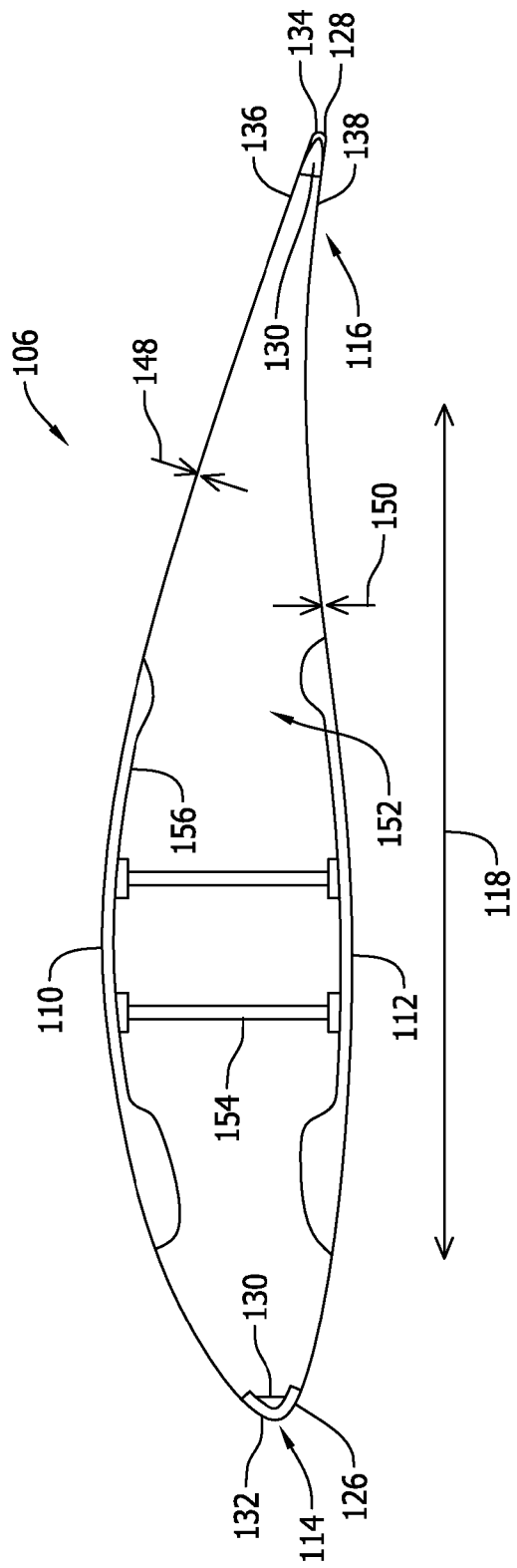
FIG. 3 is a cross-sectional view of the blade shown in FIG. 2, and taken along line 3-3 shown in FIG. 2.

FIG. 3 is a cross-sectional view of blade 106 taken along line 3-3 (shown in FIG. 2). In the exemplary embodiment, first and second members 110 and 112, respectively, are joined together by a leading edge joint 126 at leading edge 114 and by a trailing edge joint 128 at trailing edge 116. Leading edge joint 126 is formed from an adhesive bond 130 and a leading edge structural member 132 such that leading edge joint 126 has a pre-determined strength and rigidity. In the exemplary embodiment adhesive bond 130 is a two-part bonding paste that bonds first and second members 110 and 112 together. In alternative embodiments, adhesive bond 130 is any other suitable type of bonding material that enables blade 106 to function as described herein. Leading edge structural member 132 is formed from a rigid fiberglass material that enhances the strength of leading edge 114. In alternative embodiments, leading edge structural member 132 is any other suitable type of rigid material that enables blade 106 to function as described herein.

Trailing edge joint 128 is formed with adhesive bond 130 and an edge cap 134. Edge cap 134 is a rigid fiberglass member that is pre-formed into a shape that substantially mirrors designed shape and size of trailing edge 116. Furthermore, edge cap 134 is coupled to a trailing edge 136 of first member 110 and to a trailing edge 138 of second member 112 so as to define trailing edge 116. Edge cap 134 defines an external bonding bridge that is the primary seal between first and second members 110 and 112. In the exemplary embodiment, edge cap 134 is generally V-shaped and includes a first leg 140 having a thickness 142 and an opposite second leg 144 having a thickness 146 (shown in FIG. 4). Additionally, first member 110 has a thickness 148 and second member has a thickness 150. First leg 140 of edge cap 134 is coupled to trailing edge 136 of first member 110 and second leg 144 of edge cap 134 is coupled to trailing edge 138 of second member 112 such that legs 140 and 144 are substantially flush with respective first and second members 110 and 112. The strength of trailing edge joint 128 at least partially depends on the width of adhesive bond 130 extending from trailing edge 116 towards leading edge 114 in chord direction 118. In alternative embodiments, edge cap 134 is any other suitable type of rigid material and/or shape that enables blade 106 to function as described herein.

First and second members 110 and 112 also define an internal cavity 152 with structural members positioned therein. For example, in the exemplary embodiment, spar cap 154 extends between first and second members 110 and 112 in cavity 152, and shear web 156 extends between root portion 120 and tip portion 122 in cavity 152. In alternative embodiments, blade 106 has any other suitable configuration that enables wind turbine 100 to operate as described herein.

Figure 4:
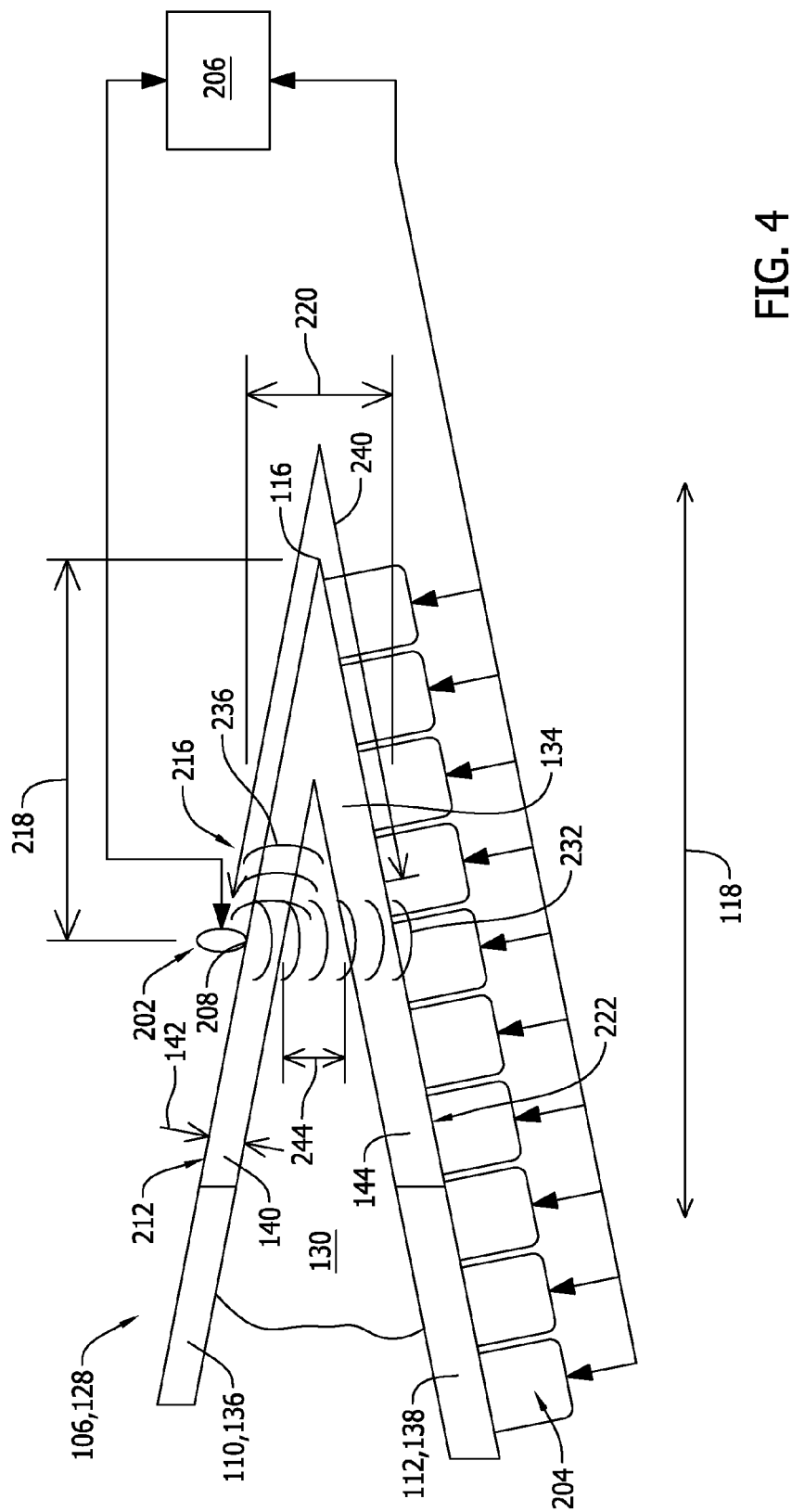
FIG. 4 is a schematic view of an exemplary bond width determination system coupled to the trailing edge joint shown in FIG. 3.
Figure 5:
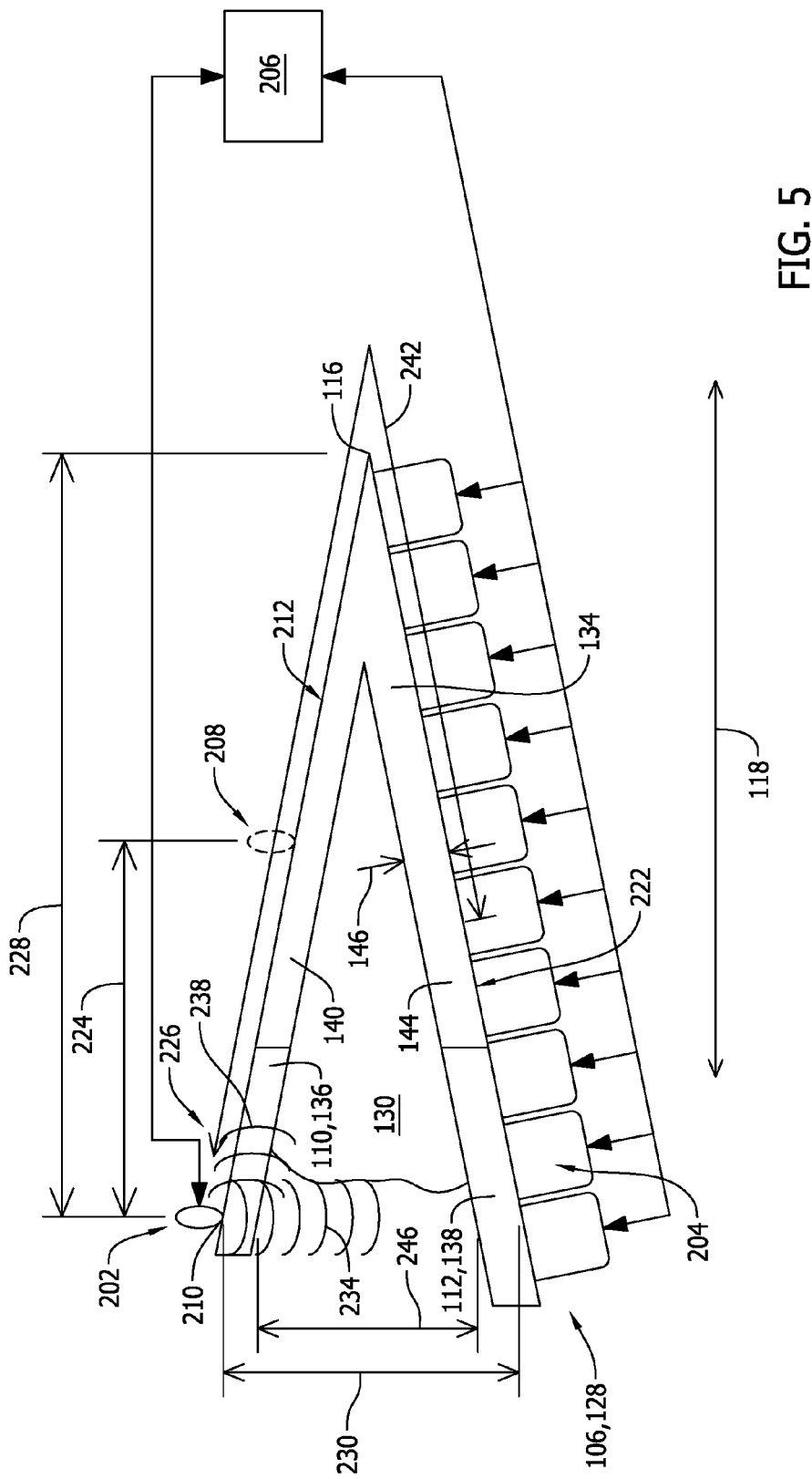
FIG. 5 is another schematic view of the exemplary bond width determination system shown in FIG. 4.

FIGS. 4 and 5 are schematic views of an exemplary bond width determination system 200 coupled to trailing edge joint 128 on blade 106 (shown in FIG. 3). In the exemplary embodiment, system 200 includes a sound wave device 202 and a plurality of sensors 204 that are operatively coupled to a controller 206. Sound wave device 202 is shown at a first location 208 in FIG. 4 and at a second location 210 in FIG. 5. Sound wave device 202 is positioned adjacent to a first side 212 of trailing edge joint 128. At first location 208, sound wave device 202 is operable to generate a first sound wave 216 that propagates through trailing edge joint 128. First location 208 is defined on first side 212 at a first distance 218 measured substantially parallel to chord direction 118 from trailing edge 116. Additionally, at first location 208, a first thickness 220 is defined as a distance extending from first location 208 on first side 212 to an opposite second side 222 that is perpendicular to chord direction 118. In the exemplary embodiment, first side 212 is defined by first member 110 and first leg 140 of edge cap 134, and second side 22 is defined by second member 112 and second leg 144 of edge cap 134. In alternative embodiments, each of first side 212 and second side 222 is defined by any suitable structure that enables blade 106 to function as described herein.

At second location 210, sound wave device 202 is operable to generate a second sound wave 226 that propagates through trailing edge joint 128. Second location 210 is defined on first side 212 at a second distance 228 measured substantially parallel to chord direction 118 from trailing edge 116. Second distance 228 is a predetermined offset distance 224 from first location 208 and substantially parallel to chord direction 118. Additionally, at second location 210, a second thickness 230 is defined as the distance from second location 210 on first side 212 extending to opposite second side 222 and substantially perpendicular to chord direction 118. In the exemplary embodiment, sound wave device 202 is a tapper that is capable of generating sound waves that penetrate and propagate through blade 106. Additionally or alternatively, sound wave device 202 may be any other suitable device that enables system 200 to function as described herein.

Additionally, it should be understood that although system 200 is described and shown with respect to trailing edge joint 128 of blade 106, system 200 may be used on other bonded areas, such as leading edge joint 126.

System 200 also includes sensors 204 that receive first and second sound waves 216 and 226 at second side 222 of trailing edge joint 128. In the exemplary embodiment, sensors 204 are coupled to second side 222 and arranged in series extending from proximate to trailing edge 116 towards leading edge 116 along chord direction 118. In alternative embodiments, sensors 204 are arranged in any other suitable orientation that enables system 200 to function as described herein. In the exemplary embodiment, sensors 204 are operable to receive sound wave information after transmission through blade 106 from sound generation device 202, and convey the received sound wave information to controller 206.

In the exemplary embodiment, system 200 includes a single sound wave device 202 that is movable from first location 208 to second location 210. Alternatively or additionally, system 200 includes a plurality of sound wave devices 202 that generate sound waves 216 and 226 at different locations. Moreover, in the exemplary embodiment, system 200 includes a plurality of sensors 204 arranged opposite sound wave device 202 with respect to blade 106. Alternatively or additionally, system 200 includes a single sensor 204 that is movably positionable along second side 222 to locations opposite first location 208 and second location 210.

In the exemplary embodiment, system 200 is operable to identify a presence or absence of adhesive bond 130 adjacent first and second locations 208 and 210 from first and second sound waves 216 and 226 transmitted through trailing edge joint 128. Specifically, sound wave device 202 generates sound waves 216 and 226 that propagate through trailing edge joint 128, such as through at least one of first member 110, second member 112, edge cap 134, and/or adhesive bond 130. Sensors 204 measure a travel time of sound waves 216 and 226 through trailing edge joint 128. From the measured elapsed time values, controller 206 calculates a theoretical thickness of trailing edge joint 128 based on known material properties, such as a speed of sound through first member 110, second member 112, edge cap 134, and/or adhesive bond 130, and compares the calculated theoretical thickness with a measured thickness, such as first thickness 220 and/or second thickness 230. When the calculated theoretical thickness at a location is approximately equal to the actual thickness, system 200 determines that adhesive bond 130 is present at that location. When the calculated theoretical thickness is not approximately equal to the actual thickness at a location, system 200 determines that adhesive bond 130 is absent, or not present, at that location. Thus, system 200 at least partially determines the bond width from trailing edge 116 along chord direction 118. For example, if system 200 determines that adhesive bond 130 is present adjacent to first location 208 and is absent adjacent to second location 210, system 200 defines the bond width as at least first distance 218 adjacent first side 212.

More specifically, in the exemplary embodiment, system 200 generates first sound wave 216 from sound wave device 202 at a first location 208 on blade 106 at first side 212. Sensors 204 receive first sound wave 216 and system 200 determines that adhesive bond 130 is present adjacent first location 208. System 200 also generates second sound wave 226 from sound wave device 202 at second location 210 on blade 106 at first side 212. Sensors 204 receive second sound wave 226 and system 200 determines that adhesive bond 130 is not present adjacent second location 210, such that first distance 218 at least partially defines the width of adhesive bond 130 within trailing edge joint 128.

In some embodiments, system 200 identifies a direct sound wave and a surface sound wave. For example, first and second sound waves 216 and 226 each have at least two wave components. Direct sound waves 232 and 234, respectively, are defined by the portion of first and second sound waves 216 and 226 that primarily travel directly through trailing edge joint 128 in a direction that is substantially perpendicular to chord direction 118, and surface sound waves 236 and 238, respectively, are defined by the portion of first and second sound waves 216 and 226 that primarily travel along a surface of trailing edge joint 128, and more specifically, travel along at least one of first member 110 and first leg 140 of edge cap 134, around trailing edge 116, and along at least one of second leg 144 of edge cap 134 and second member 112.

In operation, system 200 identifies direct sound waves 232 and 234 based on the travel time and strength of the sound wave received at sensors 204. Furthermore, system 200 identifies surface sound waves 236 and 238 based on how the wave propagates through sensors 204, e.g., surface sound waves 236 and 238 are received by a sensor 204 closest to trailing edge 116 before surface sound waves 236 and 238 are received by the next closest sensor 204 to trailing edge 116. Additionally or alternatively, system 200 identifies direct sound waves 232 and 234 and surface sound waves 236 and 238 via any other method that enables system 200 to operate as described herein.

In some embodiments, system 200 filters, i.e., removes via filtering, surface sound waves 236 and 238 from the received first and second sound waves 216 and 226 and uses direct sound waves 232 and 234 to determine a width of adhesive bond 130. In the exemplary embodiment, the filtering includes, for example, sensors 204 that measure a travel time of surface sound waves 236 and 238 from first or second locations 208 and 210 to each sensor 204. Furthermore, controller 206 calculates a theoretical surface sound wave travel time from first or second locations 208 and 210 to each sensor 204. When the measured surface sound wave travel time is approximately equal to the theoretical surface wave travel time, system 200 filters the measured surface sound wave.

In certain embodiments, the theoretical surface sound wave travel time is calculated for each sensor 204 by dividing a surface distance by a speed of sound value associated with the surface member material. For example, at first location 208, a first surface distance 240 for each sensor 204 is defined as a path distance from first location 208 along first side 212 to trailing edge 116, and from trailing edge 116 to sensor 204 along second side 222. Additionally, a geometry of edge cap 134, distance 218, and the speed of sound value for each material that defines first side 212 and second side 222, such as the materials used to form first member 110, edge cap 134, and second member 112, is known by and/or stored within controller 206. Thus, the theoretical surface sound wave travel time is calculated by dividing each segment of first surface distance 240 by the speed of sound value associated with the material that forms the segment. For example, in the exemplary embodiment, first location 208 is located along edge cap 134. The theoretical surface sound wave travel time is calculated by dividing a portion of first surface distance 240 defined along edge cap 134 by a speed of sound associated with the material used to form edge cap 134, and, for sensors 204 located adjacent second member 112, dividing a portion of first surface distance 240 defined along second member 112 by a speed of sound associated with the material used to second member 112.

Similarly, a second surface distance 242 for each sensor 204 is defined as a path distance from second location 210 along first side 212 to trailing edge 116, and from trailing edge 116 to sensor 204 along second side 222. Again, the theoretical surface sound wave travel time is calculated by dividing each segment of second surface distance 242 by the speed of sound value associated with the material that forms the segment. For example, in the exemplary embodiment, second location 210 is located along first member 110. The theoretical surface sound wave travel time is calculated by dividing a portion of first surface distance 240 defined along first member 110 by a speed of sound associated with the material used to form first member 110, dividing a portion of first surface distance 240 defined along edge cap 134 by a speed of sound associated with the material used to form edge cap 134, and, for sensors 204 located adjacent second member 112, dividing a portion of first surface distance 240 defined along second member 112 by a speed of sound associated with the material used to second member 112.

Additionally or alternatively, the theoretical surface sound wave travel time is calculated by any other method that enables system 200 to operate as described herein.

In some embodiments, system 200 uses direct sound wave 232 to determine that adhesive bond 130 is present at first location 208. For example, system 200 is configured to calculate a theoretical thickness of trailing edge joint 128 of blade 106 at first location 208 based on an output of sensors 204 in response to first sound wave 216. System 200 is further configured to compare actual thickness 220 of trailing edge joint 128 at first location 208 to the calculated theoretical thickness of trailing edge joint 128. When the theoretical thickness is approximately equal to actual thickness 220, system 200 indicates that adhesive bond 130 is present at first location 208.

Furthermore, in some embodiments, the actual thickness of trailing joint 128 is a known cavity thickness, such as a cavity thickness 244 at first location 208 and a cavity thickness 246 at second location 210. First cavity distance 244 is defined as the distance between the inside surface of first member 110 or first leg 140 of edge cap 134 at first location 208 and the inside surface of second member 112 or second leg 144 of edge cap 134 opposite first location 208. Second cavity distance 246 is defined as the distance between the inside surface of first member 110 or first leg 140 of edge cap 134 at second location 210 and the inside surface of second member 112 or second leg 144 of edge cap 134 opposite second location 210. For example, first and second cavity distances 244 and 246 may be determined by subtracting the thickness of first and second member 110 and 112 and/or edge cap 134 from the measured actual blade thickness 230 and 220. Additionally or alternatively, first and second cavity distances 244 and 246 can be determined by any other method that enables system 200 to operate as described herein.

In certain embodiments, calculating the theoretical thickness includes measuring the direct sound wave travel time from the first or second locations 208 and 210 to sensors 204, subtracting a known travel time through first side 212 and second side 222, and multiplying the remainder by a speed of sound value associated with adhesive bond 130. For example, in the exemplary embodiment, first direct sound wave 232 at first location 208 propagates through thickness 142 of first leg 140 and thickness 146 of second leg 144. In the exemplary embodiment, thickness 142 of first leg 140 and thickness 146 of second leg 144 are approximated as the nominal thickness without regard to the angle first and second legs 140 and 144 are positioned relative to chord direction 118. Additionally or alternatively, thickness 142 of first leg 140 and thickness 146 of second leg 144 are distances measured normal to chord direction 118. As described above, each of first leg 140 and second leg 144 is associated with a known speed of sound value, thus, a time for first direct sound wave 232 to traverse thickness 142 and thickness 146 can be subtracted from the measured direct sound wave travel time. The theoretical thickness of adhesive bond 130 is determined by multiplying the remainder by the speed of sound value associated with adhesive bond 130. Because adhesive bond 130 is present adjacent first location 208, the theoretical value is approximately equal to known cavity thickness 244 of trailing edge joint 128 at first location 208, indicating that adhesive bond 130 is present adjacent first location 208. Additionally or alternatively, a theoretical thickness associated with trailing edge joint 128 can be calculated by any other method that enables system 200 to operate as described herein.

In other embodiments, system 200 uses the measured direct sound wave travel time to determine that adhesive bond 130 is present at first location 208 by comparing a theoretical direct sound wave travel time. For example, a theoretical direct sound wave travel time is calculated by dividing each member thickness by the speed of sound value associated with the material that forms the member. For example, in the exemplary embodiment, first location 208 is located along edge cap 134. The theoretical direct sound wave travel time is calculated by dividing the thickness of first and second legs 140 and 144 by a speed of sound associated with the material used to form edge cap 134, and, for adhesive bond 130, dividing first cavity distance 244 by a speed of sound associated with the material used for adhesive bond 130. When the measured direct sound wave travel time is approximately equal to the theoretical direct sound wave travel time, system 200 will determine that adhesive bond 130 is present at first location 208.

Similarly, in certain embodiments, system 200 uses direct sound wave 234 to determine that adhesive bond 130 is not present at second location 210. For example, second direct sound wave 234 at second location 210 propagates through thickness 148 of first member 110 and thickness 150 of second member 112 at trailing edge joint 128. In the exemplary embodiment, thickness 148 of first member 110 and thickness 150 of second member 112 are approximated as the nominal thickness without regard to the angle first and second members 110 and 112 are positioned relative to chord direction 118. Additionally or alternatively, thickness 148 of first member 110 and thickness 150 of second member 112 are distances measured normal to chord direction 118. As described above, each of first member 110 and second member 112 is associated with a known speed of sound value, thus, a time for second direct sound wave 234 to traverse thickness 148 and thickness 150 can be subtracted from the measured direct sound wave travel time. The theoretical thickness of adhesive bond 130 is determined by multiplying the remainder by the speed of sound value associated with adhesive bond 130. Because adhesive bond 130 is absent adjacent second location 210, the theoretical value is substantially different from known cavity thickness 246, for example by greater than a predetermined threshold value, indicating that adhesive bond 130 is not present adjacent second location 210. Additionally or alternatively, a theoretical thickness associated with trailing edge joint 128 can be calculated by any other method that enables system 200 to operate as described herein.

In other embodiments, system 200 uses the measured direct sound wave travel time to determine that adhesive bond 130 is not present at second location 210 by comparing a theoretical direct sound wave travel time. For example, a theoretical direct sound wave travel time is calculated by dividing each member thickness by the speed of sound value associated with the material that forms the member. For example, in the exemplary embodiment, second location 210 is located along first member 110. The theoretical direct sound wave travel time is calculated by dividing the thickness of first and second members 110 and 112 by a speed of sound associated with each material used to form first and second members 110 and 112, and, for adhesive bond 130, dividing second cavity distance 246 by a speed of sound associated with the material used for adhesive bond 130. When the measured direct sound wave travel time is not approximately equal to the theoretical direct sound wave travel time, system 200 will determine that adhesive bond 130 is not present at second location 210.

In the exemplary embodiment, when it is determined that adhesive bond 130 is not present at second location 210, the adhesive bond width is at least partially defined as first distance 218 from trailing edge 116. Additionally or alternatively, system 200 is configured to identify one sensor 204 that is closest to first location 208 and, from that sensor location, at least partially determine the width of adhesive bond 130. For example, one of sensors 204 that receives direct sound wave 232 earliest in time, as compared to other sensors 204, can be considered the sensor closest to first location 208. Alternatively, one of sensors 204 that receives the strongest signal from direct sound wave 232, as compared to other sensors 204, can be considered the sensor closest to first location 208. A distance, in chord direction 118, from the closest sensor 204 to trailing edge 116 at least partially defines the width of adhesive bond 130. Furthermore, in the exemplary embodiment, system 200 can be moved along span direction 124 (shown in FIG. 2) to determine the width of adhesive bond 130 at multiple positions along trailing edge joint 128.

It should be appreciated that while the exemplary bond width determination system 200 is described above with respect to bond inspection on a wind turbine blade, such as blade 106, additionally or alternatively, the exemplary bond width determination system 200 may be used for determining bond width on any other article with a connection joint having a bond. For example, bond width determination system 200 may be used with articles including, but not limited to, hollow structural sections and blades, such as wind turbine blades 106.

Figure 6:
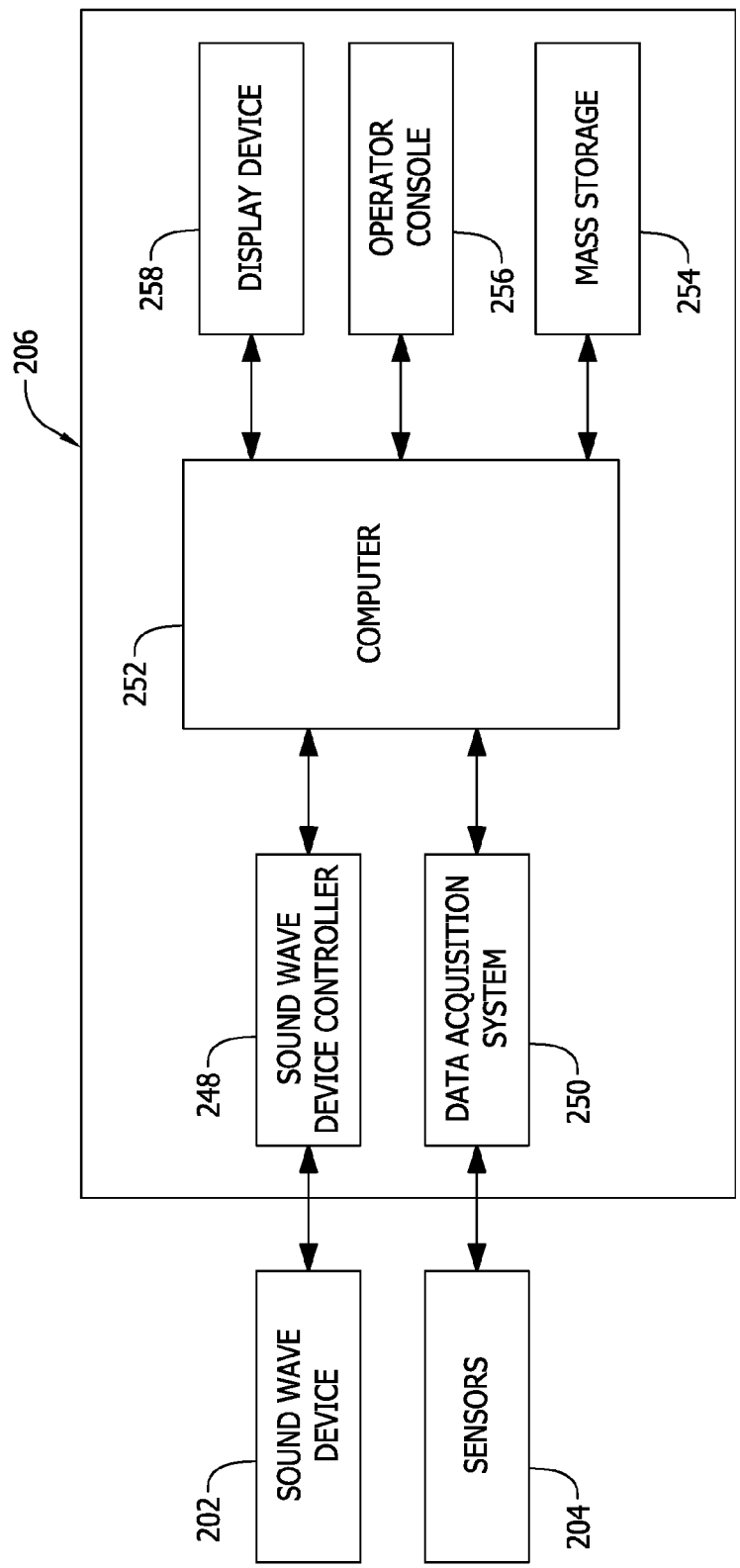
FIG. 6 is a schematic block diagram of an exemplary controller that may be used with the bond width determination system shown in FIGS. 4 and 5.

FIG. 6 is a schematic block diagram of an exemplary embodiment of controller 206 that may be used with system 200 (shown in FIGS. 4 and 5). With reference to FIGS. 4 and 5, in the exemplary embodiment, controller 206 includes a sound wave device controller 248 operatively coupled to sound wave device 202. For example, sound wave device controller 248 controls movement of sound wave device 202 in chord direction 118 along first side 212, and commands sound wave device 202 to generate sound waves, such as sound waves 216 and 226, that propagate through trailing edge joint 128. In certain embodiments, controller 206 is configured to automatically position sound wave device 202 along chord direction 118 in increments, such as offset 224, and to generate a sound wave at each incremental location to facilitate determining the width of adhesive bond 130. Additionally or alternatively, controller 206 is configured to control sound wave device 202 based on operator input. In alternative embodiments, controller 206 is not connected to sound wave device 202 and sound wave device 202 is positionable and operable manually.

In the exemplary embodiment, controller 206 also includes a data acquisition system 250 operatively coupled to sensors 204. Data acquisition system 250 acquires analog and/or digital data from sensors 204 in response to first and second sound wave 216 and 226 information along second side 222 of trailing edge joint 128.

Controller 206 also includes a computer 252. In the exemplary embodiment, computer 252 is in communication with sound wave device controller 248 and data acquisition system 250. More specifically, control signals are sent from computer 252 to sound wave device controller 248 and information is received from sound wave device controller 248 by computer 252. Computer 252 also provides commands and operational parameters to data acquisition system 250 and receives the process data from data acquisition system 250. The processed data is analyzed by computer 252, for example by comparison to reference data retrieved by computer 252 from a mass storage system 254. Additionally or alternatively, the processed data is stored by computer 252 in mass storage system 254 for subsequent retrieval and analysis. For example, but not limited to, blade geometry, speed of sound values for blade materials, offset 224 values, sensor positions, predetermined threshold values for comparing theoretical values vs measured values. An operator interfaces with computer 252 through an operator console 256, which may include, for example, a keyboard and a graphical pointing device, and receives output, such as, for example, an analysis of a condition, such as presence of adhesive bond 130, a list of control setting, and/or other information, on a display device 258.

Communication between the various elements of determination system 200 is depicted in FIG. 6 by arrowhead lines, which illustrate at least one of signal communication and mechanical operation, depending on the system element involved. Communication among and between the various system elements may be obtained through a hardwired or a wireless arrangement. Computer 252 may be a standalone computer or a network computer and may include instructions in a variety of computer languages for use on a variety of computer platforms and under a variety of operating systems. Other examples of computer 252 include a system having a microprocessor, microcontroller, or other equivalent processing device capable of executing commands of computer readable date or programs for executing a control algorithm. In order to perform the prescribed functions and desired processing, as well as the computations therefore, controller 206 may include, for example and without limitation, processor(s), memory, storage, register(s), timing, interrupt(s), communication interfaces, and input/output signal interfaces, as well as combinations including at least one of the foregoing.

Figure 7:
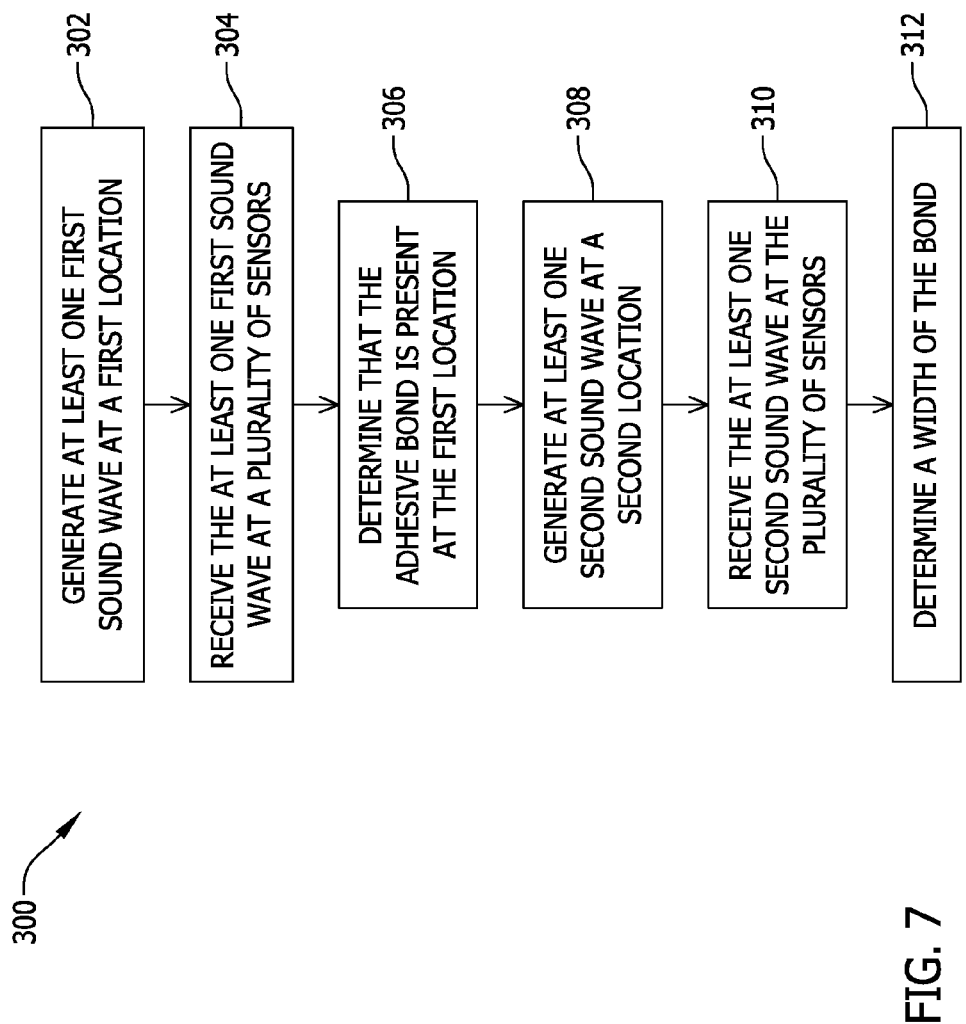
FIG. 7 is a flow diagram of an exemplary method of determining bond width on a wind turbine blade, such as the blade shown in FIG. 2.

An exemplary embodiment of a method 300 of inspecting a blade, such as blade 106, is illustrated in a flow diagram in FIG. 7. With reference also to FIGS. 1-6, exemplary method 300 includes generating 302 at least one first sound wave, such as first sound wave 216, at a first location, such as first location 208, on a first side, such as first side 212. Method 300 also includes receiving 304 the at least one first sound wave at a plurality of sensors, such as sensors 204, coupled to a second side, such as second side 222, and determining 306 that the bond, such as adhesive bond 130, is present at the first location. Method 300 further includes generating 308 at least one second sound wave, such as second sound wave 226, at a second location, such as second location 210, on the first side. Method 300 also includes receiving 310 the at least one second sound wave at the plurality of sensors and determining 312 a width of the adhesive bond.

Exemplary embodiments of methods and systems for use in determining bond width on a wind turbine blade are described above in detail. The embodiments described herein provide several advantages in testing wind turbine blades. Specifically, the methods and systems described herein facilitate non-destructive testing of wind turbine blades to determine bond width and verification of design requirements. More specifically, the methods and systems described herein are not limited by wind turbine blade materials, as sound waves propagate through a wide variety of materials. Some embodiments described herein provide advantages in that surface sound waves are filtered providing a more accurate bond width determination. Certain embodiments provide an advantage in that bond width is quickly determined and the system is mobile decreasing the costs associated with testing wind turbine blades. Thus, the methods and systems for determining bond width on a wind turbine blade described herein enable a non-material dependent and cost saving test that is non-destructive and provides reliable results.

The systems and methods described herein are not limited to the specific embodiments described herein. For example, components of each system and/or steps of each method may be used and/or practiced independently and separately from other components and/or steps described herein. In addition, each component and/or step may also be used and/or practiced with other assemblies and methods.

While the disclosure has been described in terms of various specific embodiments, those skilled in the art will recognize that the disclosure can be practiced with modification within the spirit and scope of the claims. Although specific features of various embodiments of the disclosure may be shown in some drawings and not in others, this is for convenience only. Moreover, references to "one embodiment" in the above description are not intended to be interpreted as excluding the existence of additional embodiments that also incorporate the recited features. In accordance with the principles of the disclosure, and feature of a drawing may be referenced and/or claimed in combination with any feature of any other drawing.

What is claimed is:

1. A method of inspecting a connection joint including a first side coupled to an opposite second side along a bond, extending along an edge, said method comprising:
   generating at least one first sound wave at a first location on the first side, wherein the first location is at a first distance from the edge;
   receiving the at least one first sound wave at a plurality of sensors coupled to the second side;
   determining that the bond is present at the first location;
   generating at least one second sound wave at a second location on the first side, wherein the second location is offset a predetermined distance from the first location;
   receiving the at least one second sound wave at the plurality of sensors; and
   determining a width of the bond.

2. The method according to claim 1 further comprising identifying a direct sound wave.

3. The method according to claim 1, wherein determining that the bond is present at the first location further comprises:
   calculating a theoretical thickness of the bond at the first location based on an output of the plurality of sensors in response to the at least one first sound wave; and
   comparing a first cavity distance between the first side and second side at the first location to the theoretical thickness of the bond, wherein if the theoretical thickness of the bond is approximately equal to the first cavity distance than the bond is present at the first location.

4. The method according to claim 3, wherein calculating the theoretical thickness of the bond further comprises:
   measuring a direct sound wave travel time from the first location to at least one of the sensors;
   subtracting a known travel time through at least one material, wherein the connection joint is formed from the at least one material; and
   multiplying the remaining direct sound wave travel time by a speed of sound value associated with the bond.

5. The method according to claim 1, wherein determining the width of the bond further comprises:
   calculating a theoretical thickness of the bond at the second location based on an output of the plurality of sensors in response to the at least one second sound wave; and
   comparing a second cavity distance between the first side and second side at the second location to the theoretical thickness of the bond, wherein if the theoretical thickness of the bond is different from the second cavity distance by greater than a threshold value than the bond is not present at the second location.

6. The method according to claim 5, wherein determining the width of the bond further comprises at least partially defining the width of the bond by the first distance when the bond is not present at the second location.

7. The method according to claim 1 further comprising identifying a surface sound wave.

8. The method in accordance with claim 1 further comprising filtering a surface sound wave from the at least one received first or second sound wave.

9. The method in accordance with claim 8, wherein filtering the surface sound wave comprises:
measuring a surface sound wave travel time from the first or second location to at least one of the sensors;
calculating a theoretical surface sound wave travel time from the first or second location to the at least one sensor; and
comparing the measured surface sound wave travel time and the theoretical surface sound wave travel time, wherein if the measured surface sound travel time is approximately equal to the theoretical surface sound wave travel time than the measured surface sound wave is filtered.

10. The method in accordance with claim 9, wherein the at least one sensor is located at a surface distance from the first or second location, the surface distance measured along the first side from the first or second location to the edge and further along the second side from the edge to the at least one sensor, and wherein calculating the theoretical surface sound wave travel time comprises:
dividing the surface distance by a speed of sound value associated with at least one material, wherein the connection joint is formed from the at least one first material.

11. The method in accordance with claim 1 further comprising arranging the plurality of sensors in series along a chord direction from the edge.

12. The method in accordance with claim 1 further comprising:
filtering out a surface sound wave from the at least one received first sound wave; and
identifying, based on the filtered at least one received first sound wave, one of the plurality of sensors that is closest to the first location from among at least one of the plurality of sensors that receives a direct sound wave.

13. The method in accordance with claim 12, wherein determining the width of the bond further comprises at least partially defining the width of the bond based on a distance of the closest sensor from the first edge.

14. The method in accordance with claim 12, wherein identifying the sensor that is closest to the first location further comprises identifying the sensor that is closest based on a strength of the filtered at least one received first sound wave at each of the least one of the plurality of sensors that receives a direct sound wave.

15. A method of inspecting a wind turbine blade including a first side coupled to an opposite second side along a bond, extending along an edge, said method comprising:
generating at least one first sound wave at a first location on the first side, wherein the first location is at a first distance substantially parallel to a chord direction from the edge;
receiving the at least one first sound wave at a plurality of sensors coupled to the second side, the plurality of sensors arranged in series along the chord direction;
determining that the bond is present at the first location, wherein said determining comprises:
calculating a theoretical thickness of the bond at the first location based on an output of the plurality of sensors in response to the at least one first sound wave; and
comparing a first cavity distance between the first side and second side at the first location to the theoretical thickness of the bond, wherein if the theoretical thickness of the bond is approximately equal to the first cavity distance than the bond is present at the first location;
generating at least one second sound wave at a second location on the first side, wherein the second location is offset a predetermined distance in the chord direction from the first location;
receiving the at least one second sound wave at the plurality of sensors; and
determining a width of the bond, wherein said determining comprises:
calculating a theoretical thickness of the bond at the second location based on an output of the plurality of sensors in response to the at least one second sound wave;
comparing a second cavity distance between the first side and second side at the second location to the theoretical thickness of the bond, wherein if the theoretical thickness of the bond is different from the second cavity distance by greater than a threshold value than the bond is not present at the second location; and
at least partially defining the width of the bond by the first distance when the bond is not present at the second location.

16. A system for inspecting a connection joint including a first side coupled to an opposite second side along a bond, extending along an edge, the system comprising:
a sound wave device positioned at the first side;
a plurality of sensors coupled to the second side; and
a controller coupled to said sound wave device and said plurality of sensors, said controller configured to generate at least one first sound wave from said sound wave device at a first location on the first side, wherein the first location is at a first distance from the edge, receive the at least one first sound wave at said plurality of sensors, determine that the bond is present at the first location, generate at least one second sound wave from said sound wave device at a second location on the first side, wherein the second location is offset a predetermined distance from the first location, receive the at least one second sound wave at said plurality of sensors, and determine a width of the bond.

17. The system in accordance with claim 16, wherein said controller is further configured to calculate a theoretical thickness of the bond at the first location based on an output of said plurality of sensors in response to the at least one first sound wave, and compare a first cavity distance between the first side and second side at the first location to the theoretical thickness of the bond, wherein if the theoretical thickness of the bond is approximately equal to the first cavity distance than the bond is present at the first location.

18. The system in accordance with claim 17, wherein said controller is further configured to measure a direct sound wave travel time from the first location to at least one of the sensors, subtract a known travel time through at least one material, wherein the connection joint is formed from the at least one material, and multiply the remaining direct sound wave travel time by a speed of sound value associated with the bond.

19. The system in accordance with claim 16, wherein said controller is further configured to calculate a theoretical thickness of the bond at the second location based on an output of said plurality of sensors in response to the at least one second sound wave, and compare a second cavity distance between the first side and second side at the second location to the theoretical thickness of the bond, wherein if the theoretical thickness of the bond is different from the second cavity distance by greater than a threshold value than the bond is not present at the second location.

20. The system in accordance with claim 16, wherein said controller is further configured to measure a surface sound wave travel time from the first or second location to at least one of said sensors, calculate a theoretical surface sound wave travel time from the first or second location to said at least one sensor, and compare the measured surface sound wave travel time and the theoretical surface sound wave travel time, wherein if the measured surface sound wave is approximately equal to the measured surface sound travel time than the measured surface sound wave is filtered.

* * * * *